United States Patent
Rath (10) Patent No.: US 10,094,758 B2
(45) Date of Patent: Oct. 9, 2018

(54) NOZZLE AND METHOD FOR FLOW CYTOMETRY

(71) Applicants: MASTERRIND GMBH, Verden (DE); Detlef Rath, Neustadt (DE)

(72) Inventor: Detlef Rath, Neustadt (DE)

(73) Assignee: MASTERRIND GMBH, Verden (DE)

(*) Notice: Subject to any disclaimer, the term of this patent is extended or adjusted under 35 U.S.C. 154(b) by 173 days.

(21) Appl. No.: 14/888,906

(22) PCT Filed: May 8, 2014

(86) PCT No.: PCT/EP2014/059505
§ 371 (c)(1),
(2) Date: Feb. 3, 2016

(87) PCT Pub. No.: WO2014/180973
PCT Pub. Date: Nov. 13, 2014

(65) Prior Publication Data
US 2016/0161391 A1 Jun. 9, 2016

(30) Foreign Application Priority Data

May 8, 2013 (DE) .......... 10 2013 208 584
May 17, 2013 (EP) .......... 13168370

(51) Int. Cl.
*G01N 21/00* (2006.01)
*G01N 15/14* (2006.01)
(Continued)

(52) U.S. Cl.
CPC ......... *G01N 15/1404* (2013.01); *C12M 47/04* (2013.01); *G01N 15/14* (2013.01);
(Continued)

(58) Field of Classification Search
CPC .... G01N 15/14; G01N 15/12; G01N 15/1404; G01N 2015/1236; G01N 2015/1409;
(Continued)

(56) References Cited

U.S. PATENT DOCUMENTS 3,871,770 A 3/1975 von Behrens et al.
4,983,038 A * 1/1991 Ohki .......... G01N 15/1404
356/246

(Continued)

FOREIGN PATENT DOCUMENTS

EP 0526131 A2 1/1998
EP 1238261 B1 5/2010
(Continued)

OTHER PUBLICATIONS

International Preliminary Report on Patentability and Written Opinion dated Nov. 19, 2015.
(Continued)

*Primary Examiner* — Hoa Pham
(74) *Attorney, Agent, or Firm* — Greer, Burns & Crain, Ltd.; Steven P. Fallon (57) ABSTRACT

The invention relates to a nozzle for flow cytometry, the housing of which is tapering towards an outlet and in which a feed tube is arranged for a core flow liquid, the outlet opening of which is arranged at a distance from the outlet of the housing. The outlet of the housing forms the outlet of the nozzle. The housing of the nozzle extends from its outlet, which is arranged at its first end to its opposite second end, and has an inlet for a sheath flow liquid connected with the internal volume. The nozzle is characterized in that in the housing a leading element that promotes the alignment of particles extends from both sides of the feed tube.

18 Claims, 2 Drawing Sheets

(51) Int. Cl.
*C12M 1/00* (2006.01)
*G01N 33/487* (2006.01)
*G01N 15/12* (2006.01)
*G01N 15/10* (2006.01)

(52) U.S. Cl.
CPC ... *G01N 33/487* (2013.01); *G01N 2015/1006* (2013.01); *G01N 2015/1081* (2013.01); *G01N 2015/1236* (2013.01); *G01N 2015/1409* (2013.01); *G01N 2015/149* (2013.01); *G01N 2015/1413* (2013.01); *G01N 2015/1422* (2013.01)

(58) Field of Classification Search
CPC ... G01N 2015/1006; G01N 2015/1413; G01N 2015/1415
USPC .................................. 356/335–343, 73, 246
See application file for complete search history.

(56) References Cited

U.S. PATENT DOCUMENTS

| | | | |
|---|---|---|---|
| 4,988,619 A | 1/1991 | Pinkel | |
| 6,149,867 A | 11/2000 | Seidel et al. | |
| 6,861,265 B1 | 3/2005 | den Engh | |
| 7,242,474 B2* | 7/2007 | Cox | G01N 15/1404 356/246 |
| 9,404,846 B2* | 8/2016 | Buchanan | G01N 15/1404 |
| 9,726,527 B2* | 8/2017 | Norton | G01F 1/661 |
| 2004/0050186 A1 | 3/2004 | Buchanan et al. | |
| 2009/0223279 A1* | 9/2009 | McFarland | B01D 46/06 73/28.05 |

FOREIGN PATENT DOCUMENTS

| | | |
|---|---|---|
| EP | 2522983 A2 | 11/2012 |
| WO | 199905504 | 2/1999 |

OTHER PUBLICATIONS

Dean, Phillip N., et al., "Hydrodynamic Orientation of Sperm Heads for Flow Cytometry", Biophys. J., vol. 23, Aug. 1978, pp. 7-13.

* cited by examiner

NOZZLE AND METHOD FOR FLOW CYTOMETRY

The present invention relates to a nozzle for a flow cytometer, a flow cytometer with the nozzle and a method that can be carried out with the nozzle resp. with a flow cytometer having the nozzle, for alignment of particles in a liquid flow, which has a particle-containing core flow within a sheath flow or consists thereof. In particular, the invention concerns the use of the nozzle in a method for the alignment of particles and sorting of particles depending on a property that is detected following the passage of particles through the nozzle. Here, sorting is preferably the deflection of sections of the fluid flow, in particular of drops that are formed from the fluid flow, into at least two fractions. In this embodiment, the invention relates to the production of a fraction of particles by alignment of the particles in a liquid flow with the nozzle according to the invention.

Preferably, the particles, which are aligned according to the method and are optionally sorted into fractions, have an altogether flat shape, and are symmetrical, for example, to a section plane, in such a manner that the particles have a cross-section with a first and a second dimension that is perpendicular to its longitudinal axis, wherein the cross section in the first dimension is smaller than in the second dimension. Preferred particles are biological cells, such as blood cells, in particular plate-shaped cells and non-human mammalian sperm, in particular sperm derived from a male animal, which is in particular a bovine, pig, sheep, elephant, camel, horse or a billy goat.

PRIOR ART

U.S. Pat. No. 6,149,867 describes a generic device and a method with a nozzle for sorting of mammalian sperm in sex chromosome specific sperm fractions. The method uses a flow cytometer with a nozzle, the housing of which tapers conically and in which a feed line for the core fluid containing sperm is contained, in such a manner that a core flow containing sperm flows out at the nozzle outlet, surrounded by a sheath flow.

WO 99/05504 describes a nozzle for use in a flow cytometer for sorting of sperm, which is characterized in that the housing of the nozzle in the section between the outlet opening of a feed tube for core flow liquid containing sperm has an essentially funnel-shaped inner surface, which has a first elliptical cross-section, and an adjacent axial section with elliptical cross-section, which is rotated by 90° with respect to the elliptical cross-section of the upstream section.

EP 1238261 B1 describes a nozzle for a flow cytometer for sorting of sperm, in which a feed tube for core flow liquid containing sperm arranged coaxially in a nozzle runs from a section with a cylindrical outer diameter to an essentially rectangular cross-section within a section in the shape of a truncated cone of the nozzle, wherein a tapering section of the nozzle with elliptical cross-section joins downstream of this inlet tube.

Task of the Invention

With respect to the prior art, the task of the invention is to provide an alternative nozzle for alignment of particles in a liquid flow and a method for alignment of not rotationally symmetrical particles in a liquid flow. A preferred task is to provide a nozzle, which is easy to manufacture, has in particular only components with inner surfaces, which are rotationally symmetrical and are therefore easy to produce.

General Description of the Invention

The invention solves the task with the features of the claims, in particular with a nozzle, the housing of which is tapering towards an outlet and in which a feed tube is arranged for a core flow liquid, the outlet opening of which is arranged at a distance from the outlet of the housing. The outlet of the housing forms the outlet of the nozzle. The housing of the nozzle extends from its outlet, which is arranged at its first end opposite to its second end, and has an inlet for a sheath flow liquid associated with the internal volume. The second end of the housing can be covered with a cover, in which the inlet for sheath flow liquid is optionally arranged. Preferably, the internal cross section of the housing is rotationally symmetrical resp. shaped in a circular manner and is correspondingly formed by a rotationally symmetrical inner surface, which runs at least in sections in a conical manner to the outlet. The feed tube arranged inside the housing is preferably arranged coaxially with respect to the longitudinal axis of the housing. The inlet opening of the feed tube is connected to a feed line for a particle-containing core flow liquid. The feed tube is preferably made of metal.

The nozzle according to the invention is characterized in that a leading element extends in the housing on both sides of the feed tube with a cross section, which extends further in a first dimension perpendicularly with respect to the longitudinal axis of the housing than in a second dimension arranged perpendicularly with respect to the first dimension, which second dimension is also called the thickness of the leading element. The leading element, which extends in the nozzle on both sides of the feed tube is beneficial to the alignment of particles, which are contained in the liquid flow, in particular in the core flow, in particular in such a manner that particles with a stretched cross section are brought into a common alignment, preferably into an alignment, in which the longer extension of the cross section of the particles is arranged approximately parallel to the first dimension of the leading element. The feed tube may be arranged within the leading element or formed as a bore hole within the leading element. The leading element therefore extends in the first dimension up to a smaller spacing from the inner wall of the housing, while it is further spaced apart from the inner wall of the housing in the second dimension. The leading element ends up in an edge, which limits the leading element in its first dimension and has the thickness of the second dimension. The leading element forms with the inner wall of the housing a clear cross-section, which is separated into two portions that are spaced apart by the leading element and preferably contact each other resp. converge exclusively in the area of the clear cross-section by which the leading element is spaced apart from the inner wall of the housing in the first dimension. The leading element has a thickness, which extends in the second dimension of its cross section, which is smaller than its extension along its first dimension. In the second dimension, the leading element can extend e.g. up to at maximum 70%, preferably at maximum 50%, preferably at maximum 30%, at maximum 20% or at maximum 10% with respect to the extension in the first dimension. In the second dimension, the cross-section of the leading element may change along the first dimension, in particular may decrease or increase along the first dimension from the longitudinal axis of the housing to its edge.

Along the longitudinal axis of the housing, the leading element can extend in its first dimension up to the same spacing from the longitudinal axis of the housing resp. up to the inner wall of the housing, or extend with distances that are different along the longitudinal axis of the housing, resp. up to a different distance from the inner wall of the housing. The cross section of the leading element can therefore end up in its first dimension in an edge, which is arranged along the longitudinal axis of the housing at the same distance from the inner wall of the housing, or along the longitudinal axis of the housing at a different distance from the inner wall of the housing. For example, the edge may be arranged in a section adjacent to the first end of the leading element, generally also called first end section, at a smaller spacing from the inner wall of the housing than in an adjacent section thereto, which is opposite the outlet opening of the feed tube. The edge can e.g. be arranged in the section adjacent to the first end of the leading element at an equal spacing along the longitudinal axis of the housing to the inner wall of the housing and, in the adjacent section, which is opposite the outlet opening, at a spacing from the inner wall of the housing, which increases with increasing distance from the outlet opening. Optionally, the edge is rectilinear or arched, convex or concave in sections with respect to the longitudinal axis of the housing. With respect to the second dimension, the edge may be plan, concave or convex, in particular parallel to the inner wall of the housing.

The leading element preferably has in its first end section adjacent to its first end an essentially parallel edge to the inner wall of the housing. The first end section is in particular arranged in the tapering section of the nozzle, which is adjacent to the outlet opening. This arrangement of the first end section in the tapering section of the housing allows an effective alignment of flat cells, in particular of non-human mammalian sperm. The first end section of the leading element has with increasing distance from the first end of the leading element a larger extension in the first dimension, so that the edges of the first end section run at a distance to the inner wall of the housing essentially parallel to the tapering, in particular conically converging section of the housing. The edges of the first end section may then be arched, in particular convex, and run at a distance to the tapering, in particular conically converging section of the housing. The first end section allows its arrangement in this tapering section of the nozzle. The first end section can have edges, which are at a distance from 1 to 10%, e.g. 2 to 5% of the distance between the longitudinal axis of the housing and/or of the feed tube and the housing. Adjacent to the first end section and opposite its first end, the leading element has a second end section, which tapers towards the second end. The leading element can taper in its second end section opposite the first end section, resp. at its second end, in such a manner that it flows out or ends at the feed tube. In this embodiment, the feed tube forms the carrier resp. the connection between the cover of the housing and the leading element, so that only the feed tube bears the leading element. In this embodiment, the feed tube forms a cylindrical carrier for leading element, which is spaced apart from the cover.

Between the first and the second end sections, the leading element preferably has its largest extension in the first dimension.

Optionally, the leading element has a narrow resp. sharp edge, resp. its smallest extension in the second dimension along the first and second end sections. A narrow resp. sharp edge can promote a laminar flow between the leading element and the inner wall of the nozzle.

The second end section can taper opposite the first end section up to the feed tube, resp. flow out at the feed tube. The second end section can be spaced at a distance of at least 20%, preferably at least 30%, more preferably at least 50% of the length of the feed tube within the housing, resp. the length of the feed tube between a cover of the housing and its first end, from the cover of the housing. In this embodiment, the feed tube bears the leading element alone, which preferably has a circular inner and outer cross section resp. is cylindrical. This arrangement of the leading element at a distance to the cover on the feed tube is preferred.

Alternatively, a transitional section may connect opposite the first end section to the second end section, the outer cross section of which transitional section increases and to which a cylinder section is adjacent. Therein, the cylinder section can extend up to the cover and form an annular clear cross section with the housing. The cylinder section preferably has a larger outer diameter than the extension of the second end section adjacent to the transitional section in its first dimension, so that the second end section forms a constriction in at least one of first and second dimension with the transitional section. In particular in embodiments, in which the first end section, optionally and preferably also the second end section, have a very stretched cross section, e.g. when the extension in the second dimension is 10 to 30% or at most 20% or up to 15% of the extension in the first dimension, the transitional section connects the external surfaces of the cylinder section with the ones of the leading element. The cylinder section can e.g. have an outer diameter, which is greater than the constriction and smaller than the largest extension of the leading element in its first dimension.

For the generation of a liquid flow with animal cells as particles in a core flow liquid, the inner wall of the housing may taper e.g. from a diameter of approx. 4 to 10 mm up to the outlet, which can have e.g. a diameter of 0.2 to 1 or to 0.5 mm. The leading element can extend e.g. along the longitudinal axis of the housing over 3 to 5 mm and in the first dimension from approximately 0.5 mm to 1.5 mm at the first end to approximately 3 to 5 mm at most, while it extends in the second dimension approximately by 0.5 to 1 mm on both sides of the longitudinal axis, respectively.

The leading element is preferably symmetrical to the longitudinal axis of the housing and consists in particular in two parts, which extend with their first dimensions in a common plane, in which the longitudinal axis of the housing is arranged, wherein, more preferably, the cross section of the leading element is formed symmetrically along the longitudinal axis of the housing.

The leading element causes an alignment of the particles contained in the core flow liquid according to their shape in the section between the outlet opening of the feed tube and the outlet of the nozzle. This alignment of the particles is currently attributed to the fact that the extension of the leading element in its second dimension causes different flow velocities of the sheath flow liquid, in particular over the first dimension of the leading element. It is assumed that these different flow velocities lead to an alignment of the particles, which they essentially also have after outflow from the outlet of the nozzle.

The nozzle has the advantage that the inner wall resp. the cross section of its housing may be rotationally symmetrical and can therefore be manufactured easily, e.g. by means of drilling. Correspondingly, the housing tapers by the fact that the inner wall spans a cross section that decreases towards the outlet and is in particular rotationally symmetrical about the longitudinal axis of the housing. Preferably, the cross section that is spanned from the inner wall of the housing is conical in the area adjacent to the outlet. Optionally, the cross section that is spanned from the inner wall of the housing can taper over the section, which extends between the outlet opening of the feed tube and the outlet of the housing, in particular converge conically. Optionally, the cross section that is spanned from the inner wall of the housing can taper over the section, which extends over the section between the outlet opening of the feed tube and the second end of the leading element or up to the second end of the housing, in particular adjacent to the section, which extends between the outlet opening of the feed tube and the outlet of the housing, in particular converge conically, or have another form, e.g. be cylindrical. Also the outlet can be rotationally symmetrical, in particular a round bore hole. Preferably, the nozzle has at its first end an insert made of hard material, e.g. ceramic or sapphire, in which a bore hole is formed as an outlet. The formation of the clear cross section of the nozzle, which controls the flow of the sheath flow liquid, takes place through the leading element arranged in the housing, wherein the cross section is produced by shaping the external surface of the leading element, resp. through the different extension of the leading element in its first and second dimension, which are perpendicular to the longitudinal axis and perpendicular to each other. The nozzle has therefore the advantage that the non-rotationally symmetrical surface of the leading element can be manufactured as external surface, while the inner wall of the housing can be manufactured as a rotationally symmetrical surface.

The leading element extends along the longitudinal axis of the housing from its first end up to its opposite second end, wherein the first end is arranged adjacent to the outlet opening of the feed tube or at a small distance further away from the outlet of the housing, as the outlet opening of the feed tube, e.g. by up to 10%, preferably by up to 5% or 2% of the distance from the outlet opening of the feed tube to the outlet of the housing. Preferably, the first end is arranged in the plane, in which the outlet opening of the feed tube lies. The second end of the leading element can abut to the second end of the housing or can be arranged at a distance from the second end of the housing, e.g. at a distance from 1 to 80%, preferably 10 to 50% of the extension of the housing from its outlet to its second end or to the second end of the leading element.

Preferably, the leading element extends in its first and second dimension perpendicular to the feed tube and along the longitudinal axis of the housing, wherein in particular the feed tube is arranged coaxially with respect to the longitudinal axis of the housing.

Preferably, the nozzle at the inlet opening of the feed tube has a buffer container for core flow liquid, into which a feed line for particle-containing core flow liquid discharges. Such buffer container increases the proportion of particles, which are arranged by the housing in a predetermined alignment. This is currently attributed to the fact that a buffer container reduces flow effects from the feed line, which continue into the feed tube. More preferably, the nozzle has an oscillation generator, which is attached to a wall of the buffer container for core flow liquid, which is arranged opposite the inlet opening of the feed tube. The oscillation generator is preferably a piezoelectric element that is impingeable with electric voltage. Particularly preferably, the oscillation generator, e.g. the piezoelectric element, is attached under pretension against the wall of the buffer chamber for core flow liquid, e.g. pressed against the wall of the buffer chamber by a cover arranged between the oscillation generator and the internal volume of the buffer chamber.

Preferably, the nozzle at the inlet opening of the nozzle for sheath flow liquid has a buffer container for sheath flow liquid, which is optionally arranged adjacent to the buffer container for core flow liquid, e.g. between the buffer container for core flow liquid and the second end of the housing, wherein further optionally the feed tube is led through the buffer container for sheath flow liquid. A buffer container for sheath flow liquid reduces effects of the feed line of sheath flow liquid to the flow of the sheath flow liquid in the clear cross section of the housing and increases the alignment of particles into a predetermined alignment.

The feed tube preferably has a circular internal cross section which can taper along the longitudinal axis of the housing and is preferably constant along the longitudinal axis of the housing.

The piezoelectric element serves as an oscillation generator, which preferably generates pressure waves that run perpendicular to the longitudinal axis of the housing, in order to generate a droplet flow in case of arrangement of the outlet of the housing in a gas-filled space.

A flow cytometer with the nozzle according to the invention preferably has at least one first radiation source, which is oriented towards a first section of the liquid flow coming out of the housing of the nozzle, e.g. a laser, and a first detector oriented opposite the radiation source towards the first section of the liquid flow, wherein optionally the detector generates a signal, which controls a deflection apparatus in order to deflect sections of the liquid flow depending on the detection by means of the signal, e.g. to fractionate. Optionally, the device has a second radiation source, which is oriented e.g. towards a second section of the liquid flow between the first radiation source and the nozzle, and a second detector, which is oriented towards this second section. Preferably, the second detector generates a second signal, which controls the deflection apparatus, so that sections of the liquid flow are deflected additionally depending on the second signal.

The deflection apparatus can be a pair of electrically oppositely charged plates, which are arranged on both sides of the liquid flow, and have an electric contact, which is arranged in the nozzle, in particular in the housing. Optionally, the contact can be the feed tube for core flow liquid. Preferably, the electric contact is controlled depending on the first and/or second signal, so that positive or negative charging takes place depending on the first and/or second signal. Alternatively, the deflection apparatus can be a laser directed at the liquid flow, which is set up to evaporate the liquid flow only superficially up to superficial evaporation of the liquid flow, as is described e.g. in WO2010/149739.

The method according to the invention using the nozzle resp. a flow cytometer with the nozzle has the following steps:
    providing a particle-containing core flow liquid,
    providing a sheath flow liquid,
    pumping the sheath flow liquid through the inlet opening for sheath flow liquid,
    pumping the particle-containing core flow liquid through the inlet opening of the feed tube, wherein a leading element extends along the longitudinal axis of the housing, wherein the feed tube is preferably arranged coaxially with respect to the longitudinal axis of the housing, wherein the leading element divides the clear cross section of the internal volume of the housing in two parts, and wherein the leading element extends along the longitudinal axis to a greater degree along a first dimension perpendicular to the longitudinal axis up to a distance to the inner wall of the housing than it extends in a second dimension perpendicular to the longitudinal axis and to the first dimension, flowing of sheath flow liquid through the clear cross section of the housing and flowing of core flow liquid through the feed tube, wherein the core flow liquid is contacted by the sheath flow liquid after outflow from the outlet opening of the feed tube and the particles contained in the core flow liquid are moved into a predetermined alignment, optionally allowing passage through a tapering section between the outlet opening of the feed tube and the outlet of the housing, whereby the cross section of the sheath flow liquid and the core flow liquid is reduced, and exiting of the core flow liquid surrounded by a sheath flow liquid through the outlet of the housing.

Optionally, the method contains the step of detecting a property of the particle and, further optionally, the step of treating (e.g. through laser irradiation) and/or of deflecting the particles into separated fractions resp. containers depending on a detected property.

Preferably, the housing is rotationally symmetric.

In particular preferred is a method for preparing sex-chromosome-specifically sorted fractions of non-human sperm, in which the sperm is moved through the nozzle in a predetermined alignment and is moved in this alignment before the radiation path of a detector and detected.

Optionally, the leading element is slipped onto the feed tube, in a preferably reversible resp. releasable manner, and attached e.g. at the second end of the housing. Preferably, the leading element is formed in one piece with the feed tube and attached on one end opposite its outlet opening, e.g. by means of engagement with a cover, which limits the internal volume of the housing at its second end.

The feed tube may have a circular internal cross section. Alternatively, the feed tube may have a stretched internal cross section, e.g. an elliptical or rectangular internal cross section, e.g. with rounded inner edges, wherein the longer extension of a stretched internal cross section is preferably arranged approximately parallel to the first dimension. Preferably, the leading element has a symmetry plane, through which the longitudinal axis runs, and particularly preferably the internal cross section of the feed tube extends in a symmetry plane that is shared with the leading element. A stretched internal cross section of the feed tube can e.g. have a ratio of the long to the short extension of at most 0.3 or at most 0.2.

The nozzle, preferably with an insert made of ceramic or sapphire, which forms the outlet at the first end of the housing, can consist of plastics, e.g. made of PEEK or POM, optionally of ceramic. The feed tube can consist of metal and the leading element consist of plastics, e.g. made of PEEK or POM; preferably, the feed tube is formed as a bore hole with a round cross section in the leading element, which consists of plastics, e.g. made of PEEK or POM. Preferably, the method is a method for producing fractions of non-human mammalian sperm and has the step of, after the flow of a core flow liquid containing the non-human sperm of an individual through the feed tube of the nozzle, replacing the feed tube and the leading element by another feed tube and leading element or sterilizing it before core flow liquid containing the non-human sperm of another individual is allowed to flow through the feed tube of the nozzle.

The invention will now be described more precisely by means of examples and with reference to the figures, which schematically show in FIG. 1 a nozzle according to the invention in cross section along the longitudinal axis of the nozzle, FIG. 2 a cross section of the leading element arranged in the nozzle perpendicular to the longitudinal axis of the nozzle, FIG. 3 a nozzle according to the invention without its cover and FIG. 4 A)-D) leading elements.

In the figures, the same reference numerals designate and refer to functionally equivalent elements.

Figure 1:
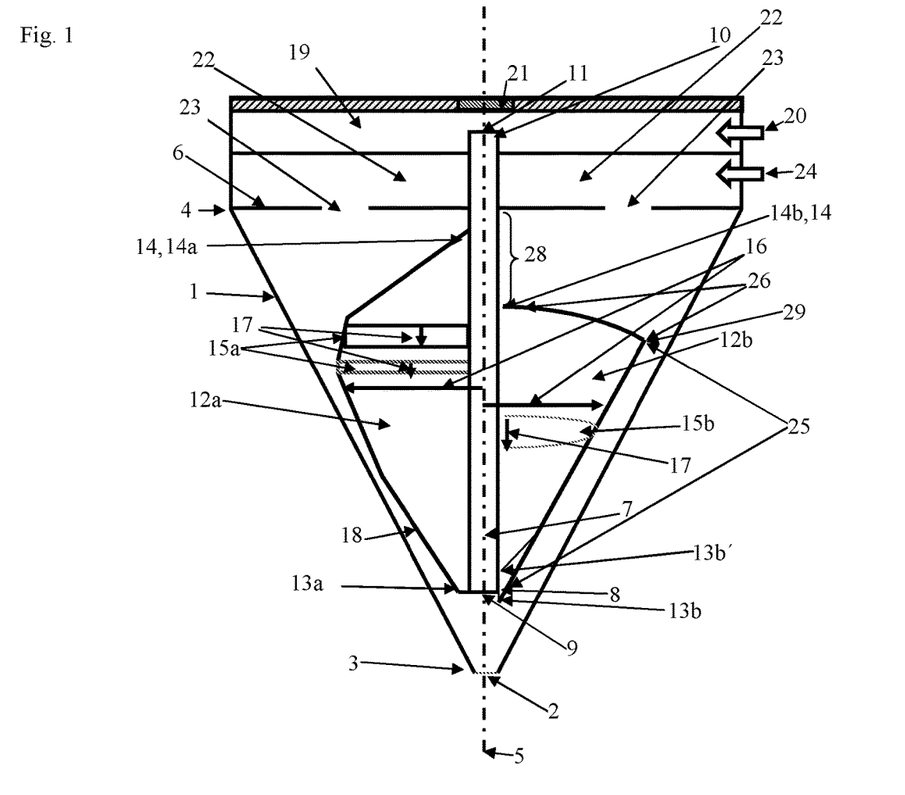

FIG. 1 shows a nozzle with a housing 1, which extends along a longitudinal axis 5 from a round outlet 2 at its first end 3 to its opposite second end 4. The second end 4 is covered by a cover 6, through which the feed tube 7 extends coaxially with respect to the longitudinal axis 5. The feed tube 7 discharges at its first end 8 into an outlet opening 9 and at its opposite second end 10 has an inlet opening 11 for a particle-containing core flow liquid. The leading element 12a, 12b is arranged at a distance to the cover 6, which closes the housing 1 at its first end 4, and is carried by the feed tube 7.

FIG. 1 shows the leading element 12a, 12b in different designs, which are represented respectively in halves on both sides of the feed tube 7, so that a design respectively extends symmetrically with respect to the longitudinal axis 5. The leading element 12a, 12b extends from its first end 13a, 13b, which is spaced apart from the first end 8 of the feed tube 7, to its second end 14a, 14b. By way of example with the leading element 12b, it is shown according to the preferred embodiment that its first end 13b can be arranged at the first end 8 of the feed tube 7 and can end flush with it. The second end 14b of the alternative leading element 12b shows that a leading element 12a, 12b can extend to a different extent along the longitudinal axis 5 of the housing 1, e.g. can be arranged at a distance farther from the outlet of the housing 1 than the outlet opening 9 or that the leading element 12b can project over the feed tube 7, as is shown at the first end 13b, or e.g. that its first end 13b' is arranged by a smaller distance farther from the outlet of the housing. The schematically drawn cross sections 15a, 15b of the leading element 12a, 12b extend perpendicular to the longitudinal axis 5 in a first dimension 16, toward which the thickness of the leading element 12a, 12b extends in the second dimension 17 perpendicular thereto. As shown by way of example with the cross section 15a, the leading element 12a may have a constant thickness in the second dimension 17, or as shown by way of example with the cross section 15b, the leading element 12b may have a cross section 15b, which changes in the second dimension 17 along the first dimension 16, e.g. decreases with increasing distance to the longitudinal axis 5.

It is shown in FIG. 1 that the leading element 12a, 12b extends in particular in a section, which is adjacent to its first end 13a, 13b along the first dimension 16 of the longitudinal axis 5 up to an approximately constant distance from the inner surface of the housing 1, resp. extends up to an edge 18 at an approximately constant distance from the inner surface of the housing 1.

The first end section 25, which is adjacent to the first end 13a, 13b of the leading element 12a, 12b, of the leading element 12a, 12b is arranged within the section of the housing 1 that conically converges towards the outlet 2. The second end section 26 is adjacent opposite the first end 13a, 13b of the leading element 12a, 12b to the first end section 25, wherein the leading element has its largest extension 29 in the first dimension, where the first and second end section 25, 26 are adjacent to each other. The design of the leading element 12a, 12b, which is such that its first end section 25 is arranged within the conically converging section of the housing 1, allows an effective alignment of cells with a flat shape, e.g. of non-human mammalian sperm, for their subsequent sorting.

FIG. 1 shows that the edge 18 of the first end section 25 runs essentially parallel and at a distance to the inner wall of the housing 1 and therein can be formed in a slightly convex manner. In general, in this embodiment, the leading element 12a, 12b can be slipped onto the feed tube 7, optionally clamped or arranged by means of a snap lock or a thread on the feed tube 7.

According to the preferred embodiment, FIG. 1 shows a nozzle with a buffer container 19 for core flow liquid, into which a supply line 20 for core flow liquid runs and to which the inlet opening 11 of the feed tube 7 is connected. A piezoelectric element 21 is attached under pretension in the buffer container 19 for core flow liquid opposite the inlet opening 11 of the feed tube 7. Furthermore, a buffer container 22 for sheath flow liquid is connected to the inlet 23 for sheath flow liquid, which discharge into the housing 1, wherein the buffer container 22 for sheath flow liquid is connected to a supply line 24 for sheath flow liquid. The buffer container 22 for sheath flow liquid is arranged between the second end 4 of the nozzle 1 and the buffer container 19 for core flow liquid, wherein the feed tube 7 is arranged through the buffer container 22 for sheath flow liquid.

Figure 2:
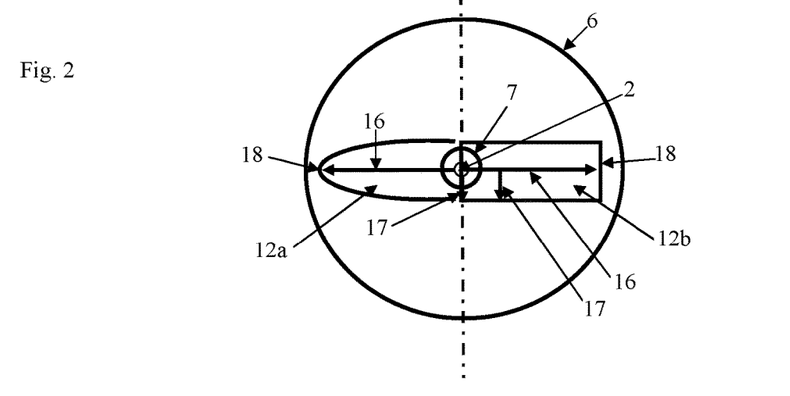

FIG. 2 shows cross sections 15a, 15b through the leading element 12a, 12b that are perpendicular to the longitudinal axis 5 of the nozzle resp. of the housing 1, wherein only half of the leading element 12a, 12b, which extends mirror-symmetrically towards the second dimension 17 resp. to the longitudinal axis 5. Preferably, the feed tube 7 is arranged in a circular manner about the longitudinal axis 5 of the housing 1, which lies in the intersection of the first dimension 16 with the second dimension 17. As is generally preferred, the outlet 2 of the housing 1 is arranged symmetrically with respect to the longitudinal axis 5 of the housing 1.

Figure 3:
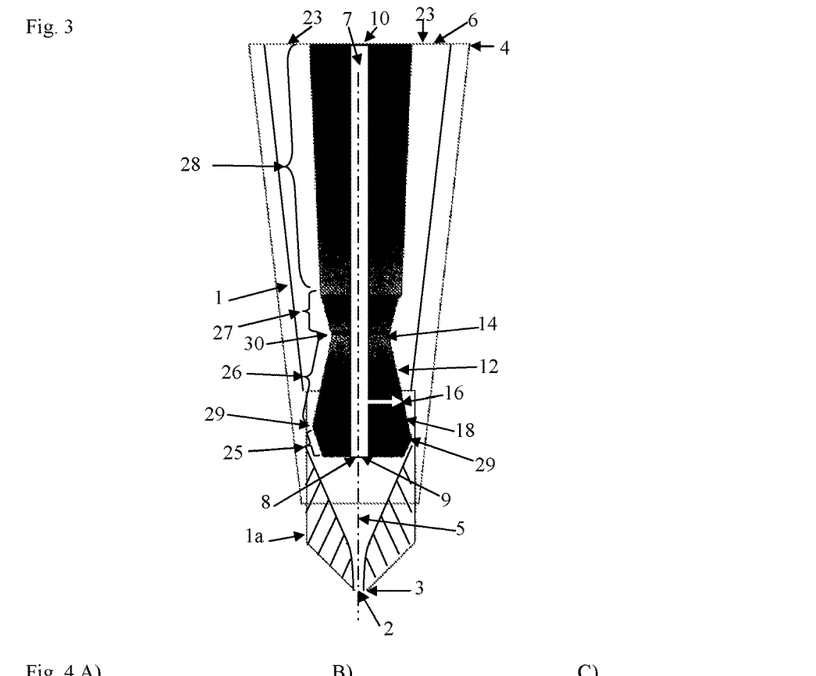

FIG. 3 shows a nozzle, in the housing 1 of which a leading element 12a is arranged, in which the feed tube 7 is carried out as a bore hole, which is arranged coaxially with respect to the longitudinal axis 5 of the housing 1. The outlet 2 of the housing 1 is formed by an insert 1a, which is shaped as a truncated cone in a section adjacent to the outlet 2 and, adjacent thereto, cylindrical. The first end section 25 is, as is generally preferred, arranged within the tapering section of the housing 1. The leading element 12a, 12b in the area adjacent to its second end section 26 has a transitional section 27, to which in turn a cylinder section 28 is adjacent. The cylinder section 28 extends across the entire length of the feed tube 7. The transitional section 27 forms a constriction 30 with the second end section 26 of the leading element 12.

Figure 4:
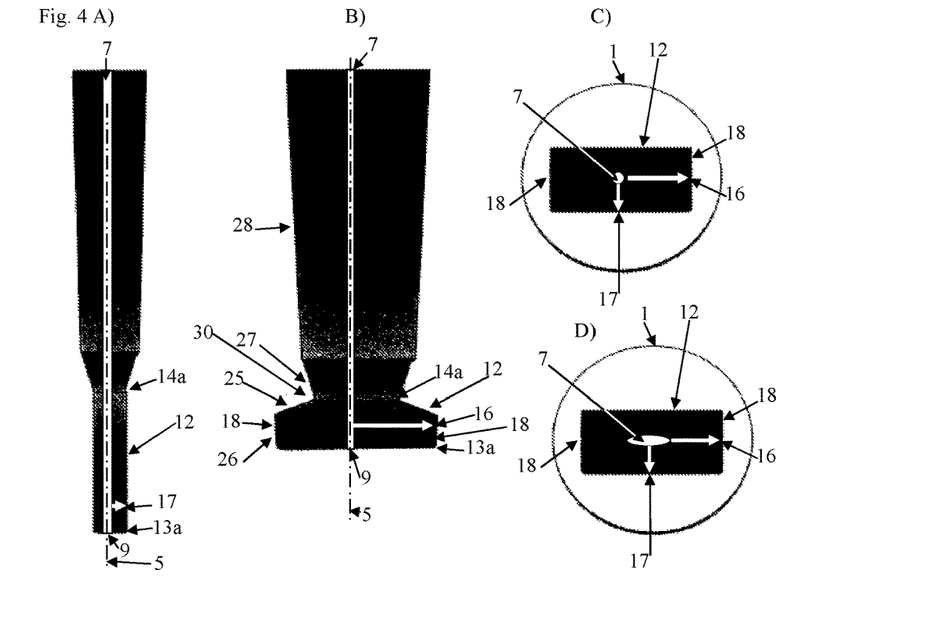

FIG. 4A) shows the leading element 12a of FIG. 3 in a reduced representation rotated by 90° about the longitudinal axis 5. It is clearly visible in FIGS. 3 and 4A) that the leading element 12a extends farther in the first dimension 16 that is perpendicular to the longitudinal axis 5 than in the second dimension 17 that is perpendicular to the longitudinal axis 5 and to the first dimension 16.

FIG. 4B) shows an optional embodiment of a leading element 12a, which extends in a section that is adjacent to the outlet opening 9 considerably farther in its first dimension 16 than in its second dimension 17, which is perpendicular to the image plane, while the cross section of the leading element 12a is tapered in the first dimension 16 in an adjacent section, which is spaced apart from the outlet opening 9.

FIG. 4C) shows a cross section 15a of a leading element 12a, which is perpendicular to the longitudinal axis 5 of the housing, in which the feed tube 7 is formed as a central bore hole with a round cross section.

FIG. 4D) shows a leading element according to FIG. 4C), in which the feed tube 7 has an elliptical internal cross section, the long extension of which is parallel to the first dimension 16 and the short extension of which is parallel to the second dimension 17. Moreover, FIG. 4D) shows that the internal cross section of the feed tube 7 has the same symmetry plane that runs through the longitudinal axis (perpendicular to the representation plane) as the cross section of the leading element 12a.

EXAMPLE 1: DETECTION OF Y-CHROMOSOME-CONTAINING SPERM IN FRESH SEMEN AND SEX-SPECIFIC SORTING

Freshly obtained bull semen was diluted in the usual manner in a diluent and incubated with a DNA-specific dye, e.g. Bisbenzimid H 33342 (Hoechst), for 30 to 60 min at a temperature of 20° C. to 40° C. and subsequently irradiated in a flow cytometer according to U.S. Pat. No. 5,125,759 or DE 10 2005 044 530 with light with the appropriate excitation wavelength for the dye. The respective emission was measured.

The alignment of the sperm was determined with a detector, which was oriented directly downstream the nozzle towards the exiting liquid flow consisting of individual droplets. The total DNA-content was determined with a further detector, which was oriented further downstream towards the liquid flow. The deflection apparatus had two oppositely charged plates on both sides of the liquid flow and a contact for electrically charging the liquid in the nozzle. This charge was fed, as is known, depending on the signal of the detector, which determines the alignment of the sperm, and the polarity of the charge depending on the signal of the detector determining the total DNA-content. In this manner, the spermatozoa were deflected depending on the detected signal through an electric field into sex-chromosome-specific fractions.

Optionally, a fluoride was added for immobilization of the sperm, e.g. into the sheath liquid or transport liquid used in the course of the sorting process, and/or before or during the addition of the dye in order to increase the penetration of the dye into the spermatozoa. Fluoride ions were added in the range of 0.1 to 100 mM, preferably of 10 nM to 10 mM. It was found that the optimal concentration of the fluoride, e.g. NaF or KF, diverged between different species and for individuals. The optimal concentration for the species is specific and could generally be determined as the concentration, which in the microscopic analysis resulted in an immobilization of at least 90% of the spermatozoa, preferably of essentially all spermatozoa. Accordingly, the present invention also refers to compositions of the sperm fractions prepared by the method according to the invention, and to methods for preparing sex-specific sperm fractions and subsequently preserving the sperm fractions of non-human mammals, each preferably in the presence of fluoride and/or anti-oxidants.

LIST OF REFERENCE SIGNS 1 housing
1a insert
2 outlet
3 first end of the housing
4 second end of the housing
5 longitudinal axis
6 cover
7 feed tube
8 first end of the feed tube
9 outlet opening
10 second end of the feed tube
11 inlet opening
12a, 12b leading element
13a, 13b, 13b' first end of the leading element
14, 14a, 14b second end of the leading element
15a, 15b cross-section of the leading element
16 first dimension
17 second dimension
18 edge
19 buffer container for core flow liquid
20 supply line for core flow liquid
21 piezoelectric element
22 buffer container for sheath flow liquid
23 inlet for sheath flow liquid
24 supply line for sheath flow liquid
25 first end section
26 second end section
27 transitional section
28 cylinder section
29 largest extension in first dimension
30 constriction

The invention claimed is:

1. A nozzle for a flow cytometer having a housing, whose internal cross-section tapers along its longitudinal axis from its second end to an outlet at its first end, and in which, for a core flow liquid, a feed tube having a circular internal cross-section is arranged, which has an inlet opening, and that discharges into an outlet opening arranged at its first end at a distance from the outlet, wherein an inlet for a sheath flow liquid is arranged at the housing, wherein the housing has an inner wall that is rotationally symmetric to its longitudinal axis, wherein a leading element, which has a first end section, which is arranged in a tapered section of the housing and the edges of which run at a distance from the inner wall of the housing, wherein the leading element extends along the longitudinal axis to a larger degree along a first dimension perpendicular to and intersecting the longitudinal axis up to a distance to the inner wall of the housing than it extends in a second dimension that is perpendicular to and intersecting the longitudinal axis and the first dimension, wherein the leading element extends from its first end, which lies in the plane of the first end of the feed tube or is offset by a distance from the first end of the feed tube, up to its second end, which is arranged at a distance from the second end of the housing, wherein the leading element at its first end has a first end section and a second end section opposite the first end and adjacent to it, which is tapered towards the second end of the leading element opposite the first end in its first dimension, wherein the leading element has its largest extension in the first dimension between the first and the second end section.

2. The nozzle according to claim 1, characterized in that the leading element is carried by the feed tube, that the leading element runs out at its second end (14, 14a, 14b) on the feed tube, and in that the distance to the second end of the leading element amounts to at least 20% of the length of the feed tube, which is arranged inside the housing.

3. The nozzle according to claim 1, characterized in that the first end (13a) of the leading element (12a) is arranged in the plane in which the outlet opening extends.

4. The nozzle according to claim 1, characterized in that the second dimension of the cross-section of the leading element decreases with increasing distance from the longitudinal axis.

5. The nozzle according to claim 1, characterized in that the leading element extends in a first end section adjacent to its first end in the first dimension up to an edge, which runs parallel to the inner wall of the housing.

6. The nozzle according to claim 1, characterized in that the feed tube extends coaxially with respect to the longitudinal axis.

7. The nozzle according to claim 1, characterized in that the feed tube is formed in the leading element as a bore hole.

8. The nozzle according to claim 1, characterized in that the feed tube is attached in the leading element.

9. The nozzle according to claim 1, characterized in that the leading element is reversibly fixable with the feed tube to a cover, which overlaps the housing at its second end.

10. The nozzle according to claim 1, characterized in that it has a buffer container for core flow liquid into which the inlet opening of the feed tube discharges.

11. The nozzle according to claim 1, characterized in that it has a buffer container for sheath flow liquid, which is connected to the inlet for sheath flow liquid.

12. A method for producing a liquid flow having a particle-containing core flow surrounded by a sheath flow by introducing a particle-containing core flow liquid into an inlet opening for core flow liquid and introducing a sheath flow liquid into an inlet opening for sheath flow liquid of a nozzle according to claim 1.

13. The method according to claim 12, characterized in that the leading element has a cross-section, which is smaller in a first dimension that is perpendicular to the longitudinal axis of the housing of the nozzle than in a second dimension that is perpendicular to the longitudinal axis and to the first dimension.

14. The method according to claim 12, characterized in that at least one property of the particles contained in the core flow is detected in the liquid flow exiting the nozzle and the particles are separated into at least two fractions depending on the detected property, or are treated differently depending on the detected property.

15. The method according to claim 12 for the production of a preparation of particles, which have a particle cross-section with a particle first dimension and a particle second dimension, wherein the particles in the particle first dimension are smaller than in the particle second dimension, characterized in that the particles are non-human mammalian sperms, the detected property is the presence of the X chromosome or Y chromosome within the sperm, and by the irradiation of the sperm depending on the detected property or deflection of the sperm depending on the detected property into at least two different fractions.

16. The nozzle according to claim 1, wherein the leading element has a thickness extending in the second dimension of its cross-section, which is smaller than the its extension along its first dimension.

17. The nozzle according to claim 1, wherein the leading element in the second dimension extends up to a maximum 50% with respect to the extension in the first dimension.

18. A nozzle for a flow cytometer having a housing, whose internal cross-section tapers along its longitudinal axis from its second end to an outlet at its first end, and in which, for a core flow liquid, a feed tube having a circular internal cross-section is arranged, which has an inlet opening, and that discharges into an outlet opening arranged at its first end at a distance from the outlet, wherein an inlet for a sheath flow liquid is arranged at the housing, wherein a leading element, which extends along the longitudinal axis to a larger degree along a first dimension perpendicular to the longitudinal axis up to a distance to the inner wall of the housing than it extends in a second dimension that is perpendicular to the longitudinal axis and to the first dimension, wherein the leading element extends from its first end, which lies in the plane of the first end of the feed tube or is offset by a distance from the first end of the feed tube, up to its second end, which is arranged at a distance from the second end of the nozzle, wherein adjacent to the second end of the leading element a transitional section is arranged, which forms a constriction with the leading element, and a cylinder section is adjacent, extending along the feed tube, opposite the leading element and adjacent to the transitional section.

* * * * *